US00PP34117P2

(12) United States Plant Patent
Gräb

(10) Patent No.: US PP34,117 P2
(45) Date of Patent: Apr. 12, 2022

(54) CHERRY TREE NAMED 'KSG 16 A'

(50) Latin Name: *Prunus avium*
Varietal Denomination: KSG 16 A

(71) Applicant: Lizenzen für Früchte und Pflanzen GmbH, Bassenheim (DE)

(72) Inventor: Hilmar Gräb, Bassenheim (DE)

(73) Assignee: Lizenxen für Früchte und Pflanzen GmbH, Bassenheim (DE)

( * ) Notice: Subject to any disclaimer, the term of this patent is extended or adjusted under 35 U.S.C. 154(b) by 0 days.

(21) Appl. No.: 17/300,410

(22) Filed: Jun. 18, 2021

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./181
See application file for complete search history.

*Primary Examiner* — Susan McCormick Ewoldt
(74) *Attorney, Agent, or Firm* — Michelle Bos Legal LLC

(57) ABSTRACT

'KSG 16 A' is a new sweet cherry tree notable for its large, intensely colored heart-shaped fruit, which has excellent flavor and texture and stores very well.

5 Drawing Sheets

Latin name: *Prunus avium.*
Variety denomination: 'KSG 16 A'.

BACKGROUND AND SUMMARY OF THE VARIETY

The new sweet cherry tree 'KSG 16 A' originated in the applicant's breeding program, where it was selected from seedlings obtained from the open pollination of female parent 'Sumtare' (not patented) by an unknown male parent at Kettig, Germany in 2004. Initial asexual propagation by grafting onto Gisela® 5 rootstock ('GI 148/2', U.S. Plant Pat. No. 9,622) rootstock was carried out at Kettig in 2006. 'KSG 16 A' was selected for its large, intensely colored heart-shaped fruit, which has excellent flavor and texture and stores very well.

'KSG 16 A' is distinguished by its late to very late bloom time as compared to the early bloom time of 'Sumtare'. 'KSG 16 A' requires a pollinator, while 'Sumtare' is self-fertile.

'KSG 16 A' is similar to sweet cherry variety 'Kordia' (not patented) in that both varieties are self-sterile and produce fruit of similar texture and firmness. 'Kordia' blooms late and is susceptible to frost, while 'KSG 16 A' blooms late to very late and is tolerant to frost damage. 'KSG 16 A' has been observed to produce higher and more consistent crop yields than 'Kordia'.

'KSG 16 A' is distinguished from related varieties 'KSG 03 A' (co-pending application Ser. No. 17/300,401) and 'KSG 24 A' (co-pending application Ser. No. 17/300,411) as shown in Table 1 below.

TABLE 1

Comparison of 'KSG 16 A' to related varieties

| | 'KSG 16 A' | 'KSG 24 A' | 'KSG 03 A' |
|---|---|---|---|
| Harvest maturity | Mid-season to late | Late | Very late |
| Tree vigor | Medium-strong | Weak | Medium-strong |

TABLE 1-continued

Comparison of 'KSG 16 A' to related varieties

| | 'KSG 16 A' | 'KSG 24 A' | 'KSG 03 A' |
|---|---|---|---|
| Fruit color | Black (black 203B) | Dark red (greyed-purple 187A) | Dark red (greyed-purple 187A) |
| Fruit shape | Heart-shaped | Broad kidney-shaped | Oblong heart-shaped |
| Bloom time | Very late | Mid-season | Early to mid-season |

The 'KSG 16 A' cherry tree has been found to exhibit its distinctive characteristics and remain stable through successive asexually propagated generations.

BRIEF DESCRIPTION OF THE PHOTOGRAPHS

The accompanying photographs, taken in 2018 at Kettig, Germany, show 12-year-old trees grown on Gisela® 5 rootstock.

Figure 1:
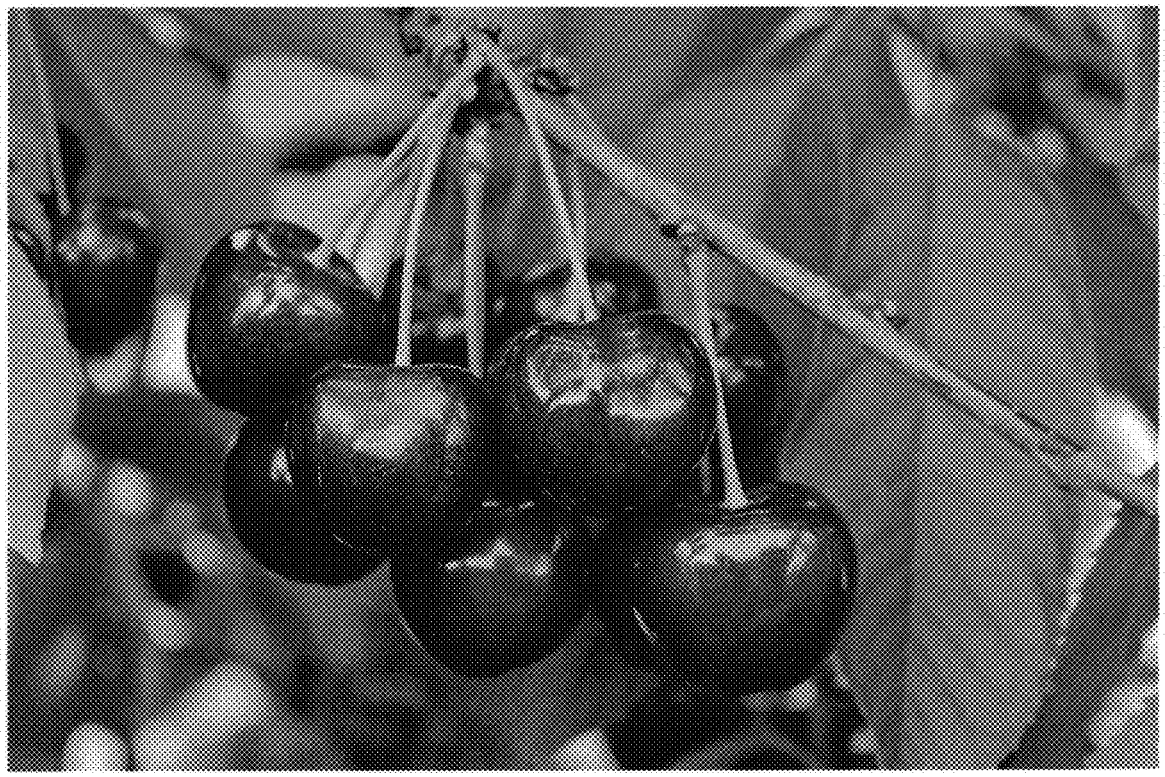
Figure 2:
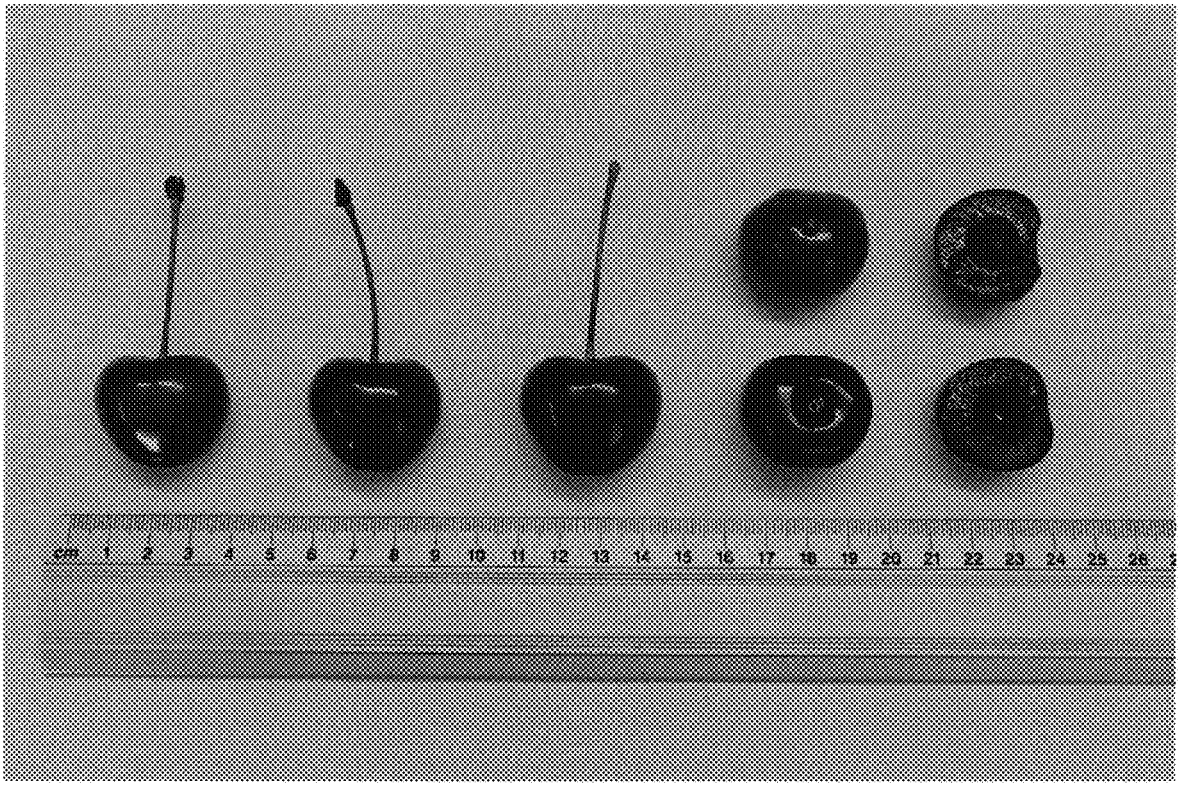
Figure 3:
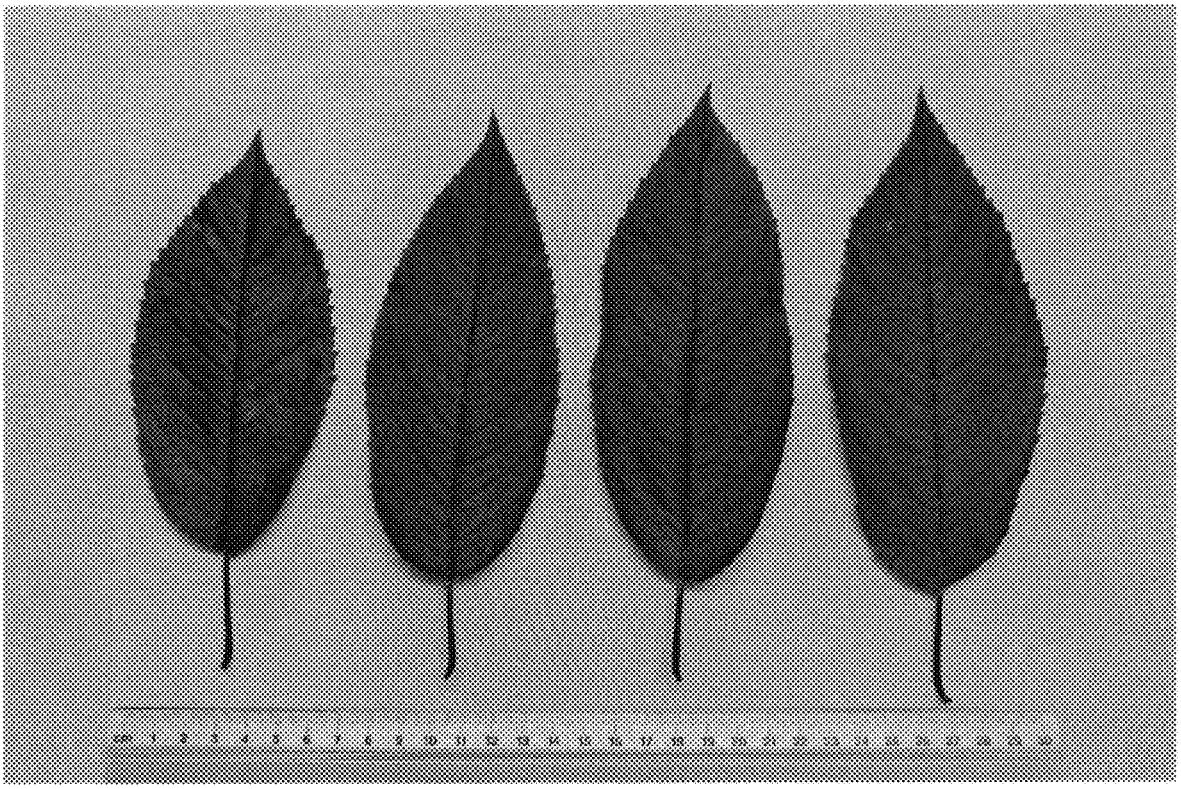
Figure 4:
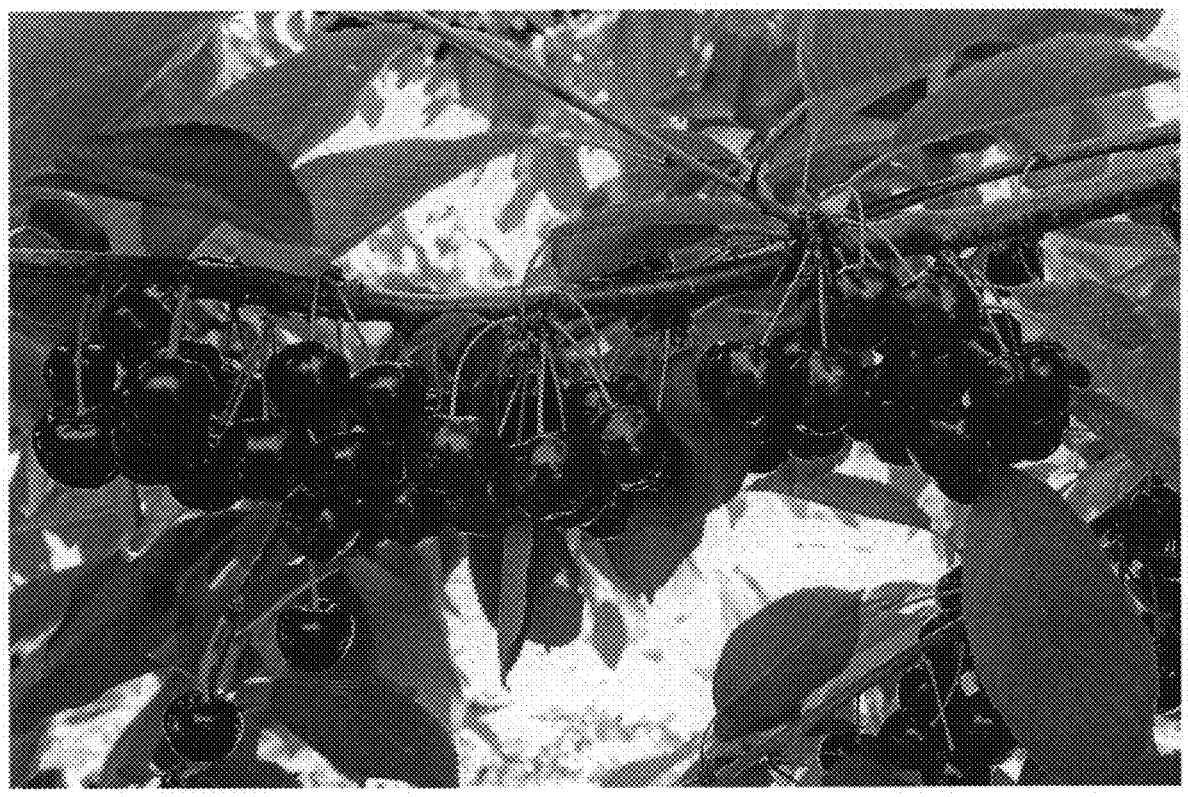
Figure 5:
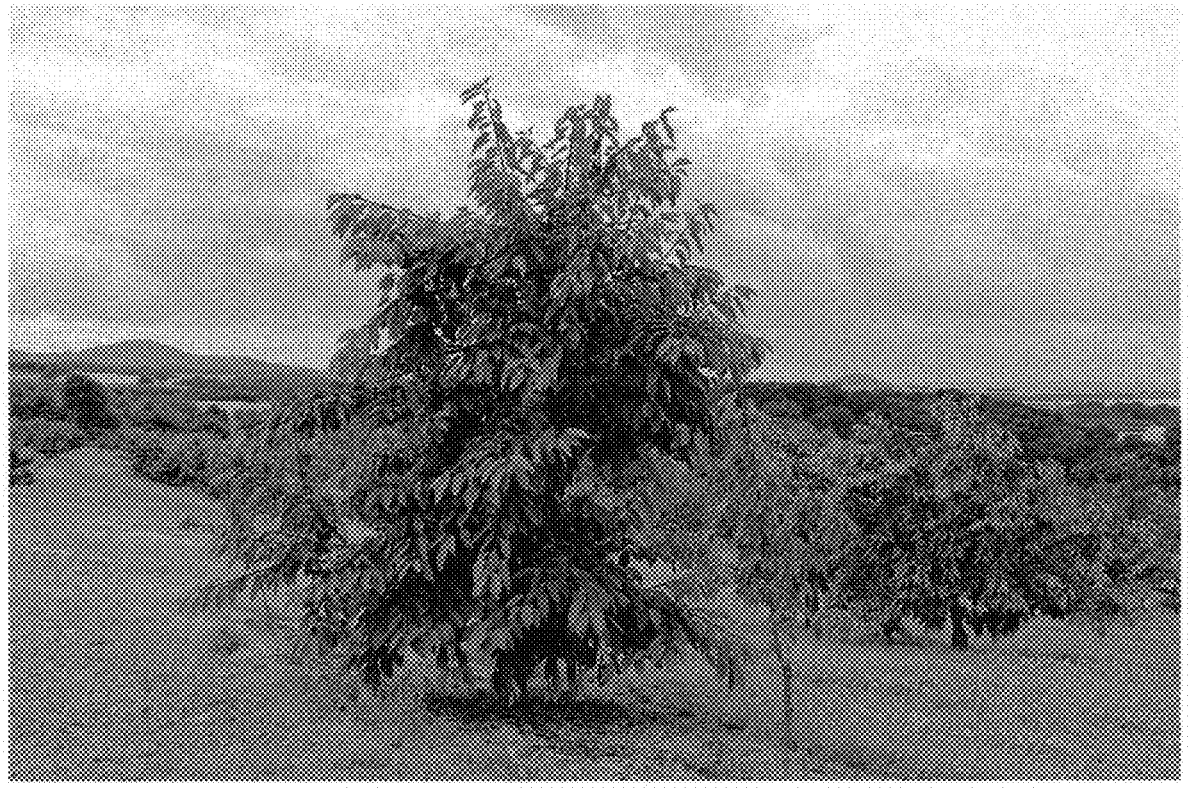

FIG. 1 shows the fruit and leaves of 'KSG 16 A';
FIG. 2 shows the fruit of 'KSG 16 A';
FIG. 3 shows the leaves of 'KSG 16 A';
FIG. 4 shows a branch, fruit and leaves of 'KSG 16 A'; and
FIG. 5 shows a tree of 'KSG 16 A'.

The colors shown in these photographs may vary with lighting conditions. Color characteristics of the claimed variety should therefore be determined with reference to the observations described herein, rather than from the photographs alone.

DETAILED BOTANICAL DESCRIPTION

The following detailed botanical description is based on observations recorded in 2018 at Kettig, Germany, of 12-year-old trees grown on Gisela® 5 rootstock. The characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Color descriptions are made with reference to The R.H.S. Colour Chart (Royal Horticultural Society, 6$^{th}$ ed.).

Tree:

*Vigor*.—Medium-strong.
*Habit, shape*.—Spreading to drooping.
*Density*.—Moderately dense.
*Height*.—2.9 m.
*Spread*.—2.6 m.
*Trunk diameter*.—11 cm at 80 cm above the graft.
*Trunk texture*.—Slightly rough.
*Bark color*.—Greyed-purple N187A.
*Lenticel length*.—2 mm to 18 mm.
*Lenticel width*.—1 mm to 3 mm, average 2 mm.
*Lenticel color*.—Greyed-orange 166C.
*Lenticel density*.—Moderate.
*Production*.—Precocious, consistent producer of optimal crop size without any over-production; 18 kg per tree (Gisela® 5 rootstock, central leader system).

One-year-old shoots:

*Diameter*.—5.5 mm.
*Surface texture*.—Smooth.
*Color*.—Greyed-orange 166C.
*Crotch angle*.—Upright to spreading.
*Buds*.—Alternate arrangement, average internode length, slightly raised, rounded tip.
*Lenticel length*.—0.5 mm to 1.5 mm.
*Lenticel width*.—0.5 mm to 0.8 mm.
*Lenticel shape*.—Oval.
*Lenticel density*.—Few.
*Lenticel color*.—Greyed-orange 164C.

Flower buds:

*Pedicel length*.—18 mm.
*Pedicel diameter*.—1.4 mm.
*Pedicel color*.—Green 143B.
*Bud length*.—10 mm.
*Bud diameter*.—6.1 mm.
*Bud shape*.—Pointed.
*Bud color*.—Greyed-orange 165A.

Flowers:

*Bloom timing*.—Very late, similar to or slightly later than 'Regina' (not patented).
*Bloom duration*.—Moderate, about 8 days.
*Pollination requirement*.—Pollinator required.
*Number of flowers per raceme*.—30 to 35, mostly 3 to 4 per unit, high density.
*Flower diameter*.—36 mm to 38 mm.
*Petals*.—5 per flower, overlapping.
*Petal length*.—17 mm.
*Petal width*.—16 mm.
*Petal shape*.—Round to slightly oval.
*Appearance*.—White, clear shell-shaped venation at base, moderately transparent.
*Margin*.—Smooth.
*Texture*.—Slightly veined.
*Petal color when opening*.—Both surfaces white NN155D.
*Petal color when fully open*.—Both surfaces white NN155D.

Sepals:

*Quantity*.—5 per flower.
*Shape*.—Elongated oval.
*Margin*.—Entire, with 3 to 4 emarginations on each side of base.
*Texture*.—Smooth.
*Length*.—7 mm to 8 mm.
*Width*.—5 mm.
*Color of upper surface*.—Green 143C.
*Color of lower surface*.—Green 139D.

Stamens:

*Quantity per flower*.—30 to 35.
*Filament length*.—10 mm.

Anthers:

*Shape*.—Rounded.
*Diameter*.—0.7 mm.
*Color*.—Greyed-orange N163A.
*Pollen color*.—Yellow-orange 21B.

Style:

*Length*.—15 mm.
*Color*.—Yellow-green 144D.

Stigma:

*Shape*.—Clearly divided in two, T-shaped.
*Color*.—Yellow 1B.

Leaves:

*Length*.—12.6 cm to 17.0 cm, average 15.0 cm.
*Width*.—5.4 cm to 7.9 cm, average 6.6 cm.
*Form*.—Elliptic with acuminate tip and obtuse base.
*Texture*.—Smooth, somewhat glossy, reticulate.
*Thickness*.—Medium.
*Margin*.—Dentate to serrate.
*Arrangement*.—Alternate.
*Pubescence of upper surface*.—None.
*Pubescence of lower surface*.—Minimal.
*Color of young leaf upper surface*.—Yellow-green 146A.
*Color or young leaf lower surface*.—Yellow-green 146B.
*Color of mature leaf upper surface*.—Green 137A.
*Color of mature leaf lower surface*.—Green 138A.
*Petiole shape*.—Rounded.
*Petiole length*.—3.6 cm.
*Petiole diameter*.—2.4 mm.
*Petiole color*.—Yellow-green 146D with anthocyanin coloration.
*Venation texture*.—Smooth on leaf upper surface; prominent on lower surface.
*Vein color*.—Green 139C on upper surface; Yellow-green 146D on lower surface.

Fruit:

*Maturity when described*.—Full maturity.
*Harvest timing*.—Mid- to late season.
*Diameter*.—28 mm to 33 mm, average 31 mm.
*Length*.—24 mm to 27 mm, average 26 mm.
*Weight*.—Average 13 g.
*Shape*.—Heart-shaped.
*Skin thickness*.—Medium.
*Skin texture*.—Smooth.
*Tendency to crack*.—Low to medium in stalk cavity.
*Skin color*.—Very dark. Young fruit deep red 53A; mature fruit black 203B with greyed-purple 187A highlights.
*Flavor*.—Sustained spicy aromatic flavor with fine acidity.
*Soluble solids*.—17° to 19° Brix at full maturity.
*Flesh color*.—Greyed-purple 187B.
*Juice color*.—Greyed-purple 187B.
*Texture*.—Firm, crisp, very juicy.

Seed:

*Height.*—10.7 mm to 12.2 mm, average 11.2 mm.
*Width.*—9.3 mm.
*Circumference.*—33 mm.
*Form.*—Wide elliptic.
*Color.*—Orange-white 159C.

Stem:

*Length.*—41 mm to 59 mm, average 50 mm.
*Diameter.*—1.1 mm to 1.4 mm, average 1.2 mm.
*Color.*—Green 141D.

Market use: Fresh consumption.
Eating quality: Very good.
Storability: Very good.
Winter hardiness: Tree and buds cold-hardy in area tested.

The invention claimed is:

1. A new and distinct cherry tree named 'KSG 16 A', substantially as illustrated and described.

* * * * *